United States Patent [19]

Albrecht

[11] Patent Number: 5,241,177
[45] Date of Patent: Aug. 31, 1993

[54] PROCESS FOR DETECTING GASEOUS SUBSTANCES

[75] Inventor: Hannes Albrecht, Berlin, Fed. Rep. of Germany

[73] Assignee: Erwin Kayser-Threde GmbH, Munich, Fed. Rep. of Germany

[21] Appl. No.: 835,584

[22] Filed: Feb. 14, 1992

[30] Foreign Application Priority Data

Feb. 14, 1991 [DE] Fed. Rep. of Germany ....... 4104785

[51] Int. Cl.$^5$ .................... G01N 21/61; G01N 21/39
[52] U.S. Cl. ................. 250/338.5; 250/341; 250/343
[58] Field of Search ............ 250/338.5, 339, 341, 250/343, 340

[56] References Cited

U.S. PATENT DOCUMENTS

| | | | |
|---|---|---|---|
| 3,856,406 | 12/1974 | Noble et al. | 250/338.5 |
| 4,425,503 | 1/1984 | Watkins et al. | 250/338.5 |
| 5,015,099 | 5/1991 | Nagai et al. | 250/338.5 |

OTHER PUBLICATIONS

Allario et al, An Exp. Concept to Meas. Stratospheric Trace Constituents by Laser Heterodyne Spect. Appl. Phys. 23, No. (1980) p. 47.

P. L. Meyer and M. W. Sigrist, "Atmospheric pollution monitoring using $CO_2$-laser photoacoustic spectroscopy and other techniques", Rev. Sci. Instrum. 61(7), Jul. 1990, pp. 1779–1807.

E. Zanzottera, "Differential Absorption Lidar Techniques in the Determination of Trace Pollutants and Physical Parameters of the Atmosphere," 1990.

*Primary Examiner*—Paul M. Dzierzynski
*Assistant Examiner*—Richard Hanig
*Attorney, Agent, or Firm*—Rothwell, Figg, Ernst & Kurz

[57] ABSTRACT

The invention relates to the field of analytical measuring technology and can be used for the detection of harmful substances in the atmosphere, for the process control of chemical gas phase reactions and for analyzing burnt off products, for example in laser surgery. The determination of the concentration of the substance to be detected ensues from the change in the modulation depth of the intensity of the irradiation of a laser operating according to the longitudinal two-mode-operation upon passage thereof through the gaseous medium to be analyzed.

3 Claims, No Drawings

PROCESS FOR DETECTING GASEOUS SUBSTANCES

BACKGROUND OF THE INVENTION

1. Field of the Invention

The invention relates to the field of analytical measuring technology and serves for detecting gaseous substances by absorbing preferably of IR-laser radiation. It can be used for detecting harmful substances in the atmosphere, for the process control of chemical phase reactions and for analyzing burn-up products, for example in laser surgery.

2. Description of the Related Art

An overview of known processes for detecting gaseous substances as well as a discussion of the advantages of spectroscopic and specifically laser spectroscopic processes can be found, for example, in P. L. Meyer and M. W. Sigrist Rev. Sci. Instrum. 61(7), July 1990, p. 1779 (named MS in the following). For detection, spectroscopic processes use the different absorption behaviour of the molecules, which, for example, results from the structure of the oscillation-rotation-spectrum in the infra-red spectral region. The weakening of the optical signal on a certain wave length is registered after passage through a gaseous medium, or the light energy absorbed in the medium, for example by means of an opto-ocoustic-detector (MS). In addition to absorption on a wavelength which is characteristic for the substance to be detected, one uses the differential absorption. In this case, the medium to be examined is irradiated by light at several and mostly two wavelengths either simultaneously or in following short sequence and the different absorption behaviour for the different wavelengths is used for the analysis. The DIAL-method is known, the differential absorption with LIDAR, in which two laser pulses of two different wavelengths are transmitted simultaneously or following in short sequence, one of the wavelengths being in resonance with the substance to be detected while the other wave length is not absorbed by this substance. The signals of both wavelengths scattered back by the aerosols in the air and then received again are differentiated and in this way, the concentration of the substance to be detected and the location at which this substance is located is localized via the travel time of the light pulse.

For detection in the infra-red spectral region, molecular gas lasers, specifically $CO_2$ are used as the light transmitting source, and for the various wavelengths, laser lines of different oscilation-rotation transitions of the lasing molcules are used.

However, the absorption lines of different substances in the infrared region often lie close to one another so that although the absorption on a laser line is different, it is determined by different substances, which greatly limits the selectivity of this method. Moreover, although the absorption spectra are structured, they are wide. If a different substance to that which is to be detected only has a low net absorption but a considerably greater concentration on the resonance line of the substance to be detected, both substances cannot be differenciated from one another by means of the absorption. On account of the absorption of water vapor with this method, these interferences have the effect that many substances in the atmosphere cannot be detected and that for many other substances, the minimal detectable concentration in the atmosphere is greatly limited (MS).

SUMMARY OF THE INVENTION

It is an object of the invention to develop a process for the detection of gaseous substances by means of IR-laser irradiation in which the interferences between the absorption of the different substances are suppressed as far as possible and that the selectivity for the detection by means of IR-laser irradiation is therefore considerably increased with respect to the known detection processes.

This object is solved in accordance with the invention in that for detection, the irradiation of a laser is used which operates according to the longitudinal two-mode-operation and in which the difference of both frequencies of the modes lies in the bandwidth of the narrow resonances of the step-by-step IR-multiphoton-absorption of the substances to be detected. In this case, one of both of the frequencies is tuned to one of the mentioned narrow resonances. For detection, the change, arising as a consequence of the absorption, in the modulation depth of the intensity of the irradiation of the two-mode laser is used.

A further structuring of the absorption spectrum of the molecules is known to arise in the region of the step-by-step IR-multiphoton-absorption (IR-MA). Narrow resonances occur (I. N. Knyazev et al, Appl. Phys. 22, 429(1980)). These differenciating features are used for detection by selecting a narrow resonance in the IR-MA spectrum of the substances to be detected at which all the remaining substances do not have such a resonance. The electromagnetic waves at both frequencies of the modes are thus absorbed equally strongly by all remaining substances, while it is absorbed at different strengths by the substance to be detected as a consequence of the narrow resonance if the frequencies of the modes are appropriately tuned to the narrow resonance.

In a laser which operates according to a longitudinal two-mode-operation, a modulation of the intensity of the laser irradiation occurs on account of the interaction of the electromagnetic waves at both frequencies. The depth of the modulation is determined from the relationship of the intensities at both frequencies and changes on account of the absorption of the substance to be detected. This change is registered by a suitable detecting system. All other substances do not change this intensity relationship and consequently do not contribute to the change of the modulation depth. The absorption of the remaining substances can therefore be desirably larger than the absorption of the substance to be detected.

The invention is described in the following in more detail by means of exemplyfied embodiments.

DESCRIPTION OF THE PREFERRED EMBODIMENTS

In one of the examples, the gas mixture to be examined, for example atmospheric air, is in an absorption cell. It is either held in a stationary state or in a flowing state in this cell. For detection, the irradiation of a line-selective, variable TEA-$CO_2$ laser is used which operates stably in the longitudinal two-mode-operation, the frequency spacing of both modes amounting to approximately 0.017 $cm^{-1}$. The laser is tuned to a laser transition corresponding to the substance to be detected. If the substance to be detected, is for example, $C_2H_4$, the laser is then, for example, set to the 10P(26) transition of the $CO_2$ molecule. A portion of the laser pulse is screened by the absorption cell and directed to an optical receiver (for example a photon-drag receiver), which transforms the variation in time of the laser pulse into a suitable electrical signal which is further processed with a suitable electronic system, the modulation depth being determined and stored. After the laser pulse has irradiated through the absorption cell, the modulation depth of the intensity is newly determined in a corresponding manner and compared with the value of the irradiation in front of the cell. A computer, for example, in which the respective standard data is stored, determines the concentration of the substance to be detected from the change in the modulation depth.

In a further exemplyfied embodiment, the TEA-$CO_2$ laser described above serves as a light transmitting source in a DIAL-system. Following transmission of the laser pulse, the modulation depth of the rereceived, back-scattered signal is determined at a time $t_1$ and newly registered at a later time $t_2$. The concentration of this substance to be detected is determined from the change in the modulation depth in the distance range $R_2-R_1$ given by $t_1$ and $t_1$ from the travel time of the laser pulse. By means of this method, one goes over, so to speak from a two-wave length-DIAL to a two-frequency-DIAL. In a further different exemplyfied embodiment, the irradiation of the TEA-$CO_2$ laser described above is expanded and directed onto a receiver matrix. Each element of the matrix transforms the variation in time of the laser pulse into a suitable electrical signal which is further processed by a suitable electronic system, the modulation depth being registered and stored. The light path is arranged such that a developing gas cloud (for example the burning products in laser surgery) travel therethrough. The change in the modulation depth indicates the occurance of the corresponding substance. The receiver matrix enables the determination of the distribution of the substance in the plane perpendicular to the expansion direction of the irradiation. If the laser is additionally equipped with an apparatus for quickly varying the wavelength, several substances can be diagnosed during the expansion of the cloud.

I claim:

1. A method for detecting a gaseous substance by absorption of IR-laser radiation, comprising the steps of:
   (a) passing a longitudinal two-mode laser through a gaseous medium;
   (b) emitting radiation from said two-mode laser;
   (c) measuring a change in the modulation depth of the intensity of the radiation of said two-mode laser; and
   (d) determining the concentration of said gaseous substance based on said change of modulation depth.

2. The method of claim 1, further comprising the step of:
   maintaining the gaseous medium in one of a stationary state and a flowing state in a cell.

3. The method of claim 1, further comprising the steps of:
   directing radiation of the laser onto a receiver matrix;
   transforming, by each element of the matrix, the variation in time of the intensity of the laser radiation into a suitable electrical signal; and
   determining the modulation depth of the intensity of the laser radiation,
   wherein the gaseous medium to be analyzed penetrates the light path as a cloud.

* * * * *